US010369300B2

(12) United States Patent
De Kruijf et al.

(10) Patent No.: US 10,369,300 B2
(45) Date of Patent: Aug. 6, 2019

(54) AEROSOL GENERATOR FOR GENERATING AN INHALATION AEROSOL

(71) Applicant: Medspray Xmems B.V., Enschede (NL)

(72) Inventors: Wilhelmus Petrus Johannes De Kruijf, Enschede (NL); Wietze Nijdam, Enschede (NL); Jeroen Mathijn Wissink, Enschede (NL); Tom Vincent Huijgen, Enschede (NL)

(73) Assignee: MEDSPRAY XMEMS B.V., Enschede (NL)

( * ) Notice: Subject to any disclaimer, the term of this patent is extended or adjusted under 35 U.S.C. 154(b) by 0 days.

(21) Appl. No.: 14/772,413

(22) PCT Filed: Mar. 7, 2014

(86) PCT No.: PCT/NL2014/050136
§ 371 (c)(1),
(2) Date: Sep. 3, 2015

(87) PCT Pub. No.: WO2014/137215
PCT Pub. Date: Sep. 12, 2014

(65) Prior Publication Data
US 2016/0015912 A1    Jan. 21, 2016

Related U.S. Application Data

(60) Provisional application No. 61/774,280, filed on Mar. 7, 2013.

(30) Foreign Application Priority Data
Mar. 7, 2013    (NL) ...................................... 2010405

(51) Int. Cl.
*A61M 11/00*    (2006.01)
*A61M 11/02*    (2006.01)
(Continued)

(52) U.S. Cl.
CPC ........... *A61M 11/02* (2013.01); *A61M 11/003* (2014.02); *A61M 11/006* (2014.02);
(Continued)

(58) Field of Classification Search
CPC .. A61M 11/02; A61M 11/06; A61M 15/0005; A61M 11/003; A61M 15/0021; A61M 15/009; A61M 2205/70
See application file for complete search history.

(56) References Cited

U.S. PATENT DOCUMENTS 4,620,670 A * 11/1986 Hughes ................. A61M 15/00
128/200.21
2006/0169800 A1 * 8/2006 Rosell .................... A61M 11/06
239/418
(Continued)

FOREIGN PATENT DOCUMENTS

DE    4306458 A1    9/1994
DE    4306458 C2    6/1996
(Continued)

Primary Examiner — Gregory A Anderson
Assistant Examiner — Victoria Murphy
(74) Attorney, Agent, or Firm — Hoffmann & Baron, LLP

(57) ABSTRACT

An aerosol generator for generating an inhalation aerosol from an inhalation liquid, includes an intake duct for guiding air to a mouth of a user, and a nozzle, arranged in the intake duct for injecting the inhalation liquid into the intake duct. The nozzle is arranged for generating a Rayleigh droplet train of the inhalation liquid propagating along a droplet train propagation path. The intake duct includes at least two first orifices having at least partly opposing discharging directions extending towards the droplet train propagation path. The at least two first orifices are configured for providing respective first air streams in at least partly opposing directions so as to interact in the droplet train propagation path.

22 Claims, 7 Drawing Sheets

(51) Int. Cl.
*A61M 11/08* (2006.01)
*A61M 15/00* (2006.01)
*A61M 11/06* (2006.01)

(52) U.S. Cl.
CPC ............ *A61M 11/06* (2013.01); *A61M 11/08* (2013.01); *A61M 15/0005* (2014.02); *A61M 15/009* (2013.01); *A61M 15/0021* (2014.02); *A61M 2205/70* (2013.01); *A61M 2206/10* (2013.01); *A61M 2206/16* (2013.01); *A61M 2206/18* (2013.01)

(56) References Cited

U.S. PATENT DOCUMENTS

| | | |
|---|---|---|
| 2011/0005517 A1 | 1/2011 | Boeck et al. |
| 2011/0048414 A1 | 3/2011 | Hoekman et al. |
| 2011/0048415 A1 | 3/2011 | Zierenberg et al. |

FOREIGN PATENT DOCUMENTS

| | | |
|---|---|---|
| GB | 2279879 A | 1/1995 |
| WO | 93/04718 A1 | 3/1993 |
| WO | 00/50112 A | 8/2000 |
| WO | 01/38002 A1 | 5/2001 |
| WO | 2008/138936 A2 | 11/2008 |
| WO | 2011/157561 A1 | 12/2011 |

* cited by examiner

| P | -1 kPa | -2 kPa | -3 kPa |
|---|---|---|---|
| Q | 168 ml/s | 250 ml/s | 295 ml/s |
| MMAD | 8.5 | 7 | 6.1 |
| d^2*Q | 12100 | 12200 | 12100 |

AEROSOL GENERATOR FOR GENERATING AN INHALATION AEROSOL

CROSS-REFERENCE TO RELATED APPLICATIONS

This application is the National Stage of International Application No. PCT/NL2014/050136 filed Mar. 7, 2014, which claims the benefit of Netherlands Application No. NL 2010405, filed Mar. 7, 2013 and of U.S. Provisional Application No. 61/774,280, filed Mar. 7, 2013, the contents of all of which are incorporated by reference herein.

FIELD OF THE INVENTION

The present invention relates to an aerosol generator for generating an inhalation aerosol, an inhaler comprising such an aerosol generator and a method of testing such an aerosol generator.

BACKGROUND OF THE INVENTION

Aerosol generators for generating an aerosol for inhalation are for example used for delivery of a drug substance to a human lung.

An aerosol generator for generating an aerosol comprises a casing in which an inhalation duct is provided. A nozzle is provided in the inhalation duct to spray a quantity of the inhalation liquid into the inhalation duct. In the inhalation duct, the inhalation liquid mixes with air or with another gas or gas mixture provided in the inhalation duct so as to form an aerosol, the aerosol then leaves the aerosol generator at an exit opening for inhalation by the user, such as a patient.

WO2008/138936 describes a metered dose liquid inhaler device.

In devices for generating a liquid inhalation aerosol, several factors may play a role.

Firstly, the drug substance is to be distributed into liquid droplets having a inhalable size and small size distribution, in order to allow the droplets to propagate into the lungs of a user effectively. In general, small size distributions enable lung targeting and a more effective propagation and deposition into the deeper lung regions of a user.

Secondly, deposition of the drug substance in the upper respiratory tract (especially mouth and throat) is to be minimized, as such deposition may not be effectively absorbed.

Thirdly, retention of the drug substance in the inhalation device itself is to be limited, so as to minimize losses and prevent contamination of the inhalation device.

Fourthly, variations in particle size distribution and aerosol dose emitting the inhalation device (drug administered to the user) is required to be minimized, so as to obtain a reliable administration of the drug substance to the user. Many factors may have an effect on the dose administered to the user, such as but not being limited to: variations in droplet size, variations in deposition in the inhalation device (retention losses), variations in deposition in the mouth and throat region, variations in inhalation air speed or variations in the dosage of drug substance per administration, etcetera.

All in all, despite many efforts, existing liquid inhaler devices appear to still provide a very wide range in the amount of drug substance that is effectively administered to the various regions of the lung, limiting a therapeutic index of drugs and their therapies.

SUMMARY OF THE INVENTION

A goal of the invention is to enable a substantially constant administration of a liquid inhalation aerosol into the lung.

In order to achieve this goal, according to an aspect of the invention, there is provided an aerosol generator for generating an inhalation aerosol from an inhalation liquid, comprising:

an intake duct for guiding air to a mouth of a user, and
a nozzle, arranged for injecting the inhalation liquid into the intake duct, wherein the nozzle is arranged for generating a Rayleigh droplet train of the inhalation liquid propagating along a droplet train propagation path, and
wherein the intake duct comprises:

at least two first orifices, each of the first orifices having a discharging direction in which respective first air streams discharge from the respective first orifices, the discharging directions of the first orifices being directed towards the droplet train propagation path, the at least two first orifices being configured for providing the respective first air streams to flow from the respective orifices along the respective discharging directions to the droplet train propagation path so as to interact with each other in the droplet train propagation path.

The inventors have devised that the aerosol generator in accordance with the invention allows to vary the particle size at different inhalation air flows to enable a substantially constant lung dose at these varying inhalation velocities, as will be explained in more detail below. Thereto, first some principles that play a role in the process of an aerosol being inhaled in the lung will be explained in some more detail.

Users of an inhaler device can comfortably inhale a certain volume of air e.g. 1 to 1.5 liter. At an inhalation flow or airflow of for example 60 liters per minute (lpm), i.e. 1000 ml/s, a user or patient inhales 1.5 liter in 1.5 seconds. At a moderate air flow of e.g. 30 liters per minute, 500 ml/s, a user or patient inhales 1.5 liter in 3 seconds. At a low airflow rate of 15 liters per minute, 250 ml/s, which may be considered a normal air flow rate for tidal breathing, a user or patient inhales 1.5 liter in 6 seconds. For liquid inhaler devices a longer inhalation time may be beneficial, since the aerosol generator may, at a same liquid flow rate, deliver more liquid medication to the lung.

The velocity of the inhaled air and hence the inhalation duration, is determined by the airflow resistance of the inhaler and the negative inhalation pressure profile generated by the user. Extensive research by the inventors with healthy volunteers inhaling through different air flow resistances has indicated that users can more comfortably inhale for a longer period if the inhaler device has a moderate to high resistance. The inventors have performed extensive usability studies with moderate to high airflow resistances (15 lpm air flow at −2 kPa under-pressure, 15 lpm at 4 kPa underpressure and 15 lpm at 6 kPa underpressure). At an air flow resistance of 15 lpm at 2 kPa underpressure, 90 percent of the healthy volunteers in the study inhaled between 1 and 1.5 liter at an average inhalation air flow rate between 10 and 20 lpm.

As explained above, the droplet size distribution and inhalation velocity of air speed play a role in the deposition of the inhalation liquid in the various regions of the lungs of a user. The higher the inhalation speed, the more likely the droplets will not be able to follow the bends the inhaled aerosol makes in the mouth, throat and larynx of the user, causing a part of the droplets to deposit there and not reach the lung. The smaller the droplet size, the deeper the inhalation liquid may penetrate into the deeper regions of the lungs, and the better the inhalation liquid may be absorbed.

When the inhalation liquid is generated by for example a plain orifice nozzle in the Rayleigh regime (also referred to in this document as a Rayleigh Nozzle RN), droplets may have a primary droplet size around twice a jet diameter (Lord Rayleigh (J. W. Strutt). On the instability of jets. Proc. London Math. Soc. 10:4-13 (1878). This may allow a generation of primary droplets having a defined size and low size distribution (also referred to as a mono-disperse aerosol). The droplets leave the Rayleigh nozzle having a forward velocity. Injected in air however, the droplets at the front of the droplet train loose some of their forward velocity, while the following droplets are in their slipstream, hence loosing less velocity and then coalescing into them. Such coalescence effects increase average droplet size and size distribution. Whether or not the nozzle operates in the Rayleigh regime largely depends inhalation liquid pressure, nozzle diameter and inhalation liquid viscosity. When making use of a nozzle diameter between 1 micrometer and 5 micrometer, the nozzle will operate in the Rayleigh regime. Thus, in an embodiment, a nozzle operating in a Rayleigh regime being formed by a nozzle having a diameter between 1 micrometer and 5 micrometers.

The aerosol generator according to the invention may further comprise a pressurizing device for pressurizing the inhalation liquid, the pressurizing device having an outlet discharging into the nozzle. In order for the nozzle to operate in the Rayleigh regime, the pressurizing device may be configured for pressurizing the inhalation liquid to a pressure in a range of between 2 Bar to 60 Bar.

The inventors have realized that coalescence of the droplets that leave the Rayleigh nozzle may be reduced by injecting them in an air stream in which turbulence occurs. The droplets, when leaving the Rayleigh nozzle, have a forward propagation velocity in the direction in which the droplets are injected. The turbulence may shake the droplets out of their propagation path, while largely maintaining their propagation velocity, so that coalescence may be reduced while maintaining a principal direction of propagation of the aerosol.

The inventors have recognized that such type of turbulence may be obtained by the at least two first air streams in mutually opposing directions that mutually interact in the droplet train propagation path. The turbulence may form a substantially homogeneous turbulence. The turbulence may effectively "shake" the droplets out of their propagation path so as to avoid coalescence of successive droplets from injected via a same opening.

The turbulence is preferably as homogeneous as possible, avoiding large eddies or vortices. Air jets with high velocity gradients are known for their high turbulence content, however opposing airstreams appear to increase the turbulence with a minimum average velocity increase, thereby, in accordance with an aspect of the invention, creating air along the droplet train path with a high homogeneous turbulence content and no (or low) increase of mean aerosol velocity. The smallest length scales (also known as Kolmogorov's length scales), are preferably in the same order of magnitude or smaller than the droplets in the droplet trains, to create a maximum interaction between the droplet and the turbulent air, in order to prevent coalescence. The overall mean velocity of the aerosol may be still much lower than the velocity from the first jets (first orifices) which created the homogeneous turbulence initially.

As explained above, deposition of the inhalation aerosol in mouth, throat and lung tends to depend on the droplet size and on the inhalation flow. It has been generally known and observed that the deposition in the upper respiratory system (mouth, throat, etc) is proportional to $d^2*Q$, wherein d is a diameter of the droplets and Q is the inhalation flow. Therefore variation of inhalation flow tends to result in variation of lung deposition or lung dose.

Furthermore, the turbulence obtained may tend to avoid that—in case of a plurality of nozzle openings which generate a plurality of (e.g. parallel) injected droplet trains, for example arranged in a row or matrix configuration, the droplets from the different droplet trains collide side to side due to under-pressure in between the different droplet trains, which may result in coalescence effects increasing droplet size.

Deposition of the inhalation liquid tends to depend on the droplet size distribution and on the inhalation flow. The larger the droplet size d, the larger the deposition in mouth, throat etc. may be. A quadratic dependency of such deposition on droplet size may be observed. The larger the inhalation flow, the larger the droplet size may be. In particular, it has been observed that the deposition in the upper respiratory system (mouth, throat, etc.) may hence be proportional to $d^2*Q$, wherein d is a diameter of the droplets and Q is the inhalation flow. Thus, keeping the droplet size small may reduce deposition (hence increase the administered dose), however keeping the droplet size small the deposition remains strongly dependent on the inhalation air flow: the larger the flow, the larger the deposition in the upper respiratory tract may be, which may (even at a low, relatively constant droplet size) cause a relatively large variation in deposition in the throat, mouth etc. of a user, thereby causing a variation in the actual lung dose from user to user, as well as between successive administrations of the inhalation liquid to a same user, as the inhalation flow may vary due to differences in lung volume, differences in power and/or speed of inhalation, etc.

The inventors have devised that with the aerosol generator in accordance with the invention, a compensation effect for varying inhalation flow may be obtained which results in a more constant lung dose deposition over varying inhalation flow, as in accordance with the aerosol generator according to an aspect of the invention, higher inhalation flow may result in higher turbulence, which may tend to cause less coalescence hence resulting in a smaller particle size at least partially compensating an effect of the higher inhalation flow. Thereby, a relatively constant effective deposition in the users lungs may be obtained, showing a low effective dependency on inhalation flow.

Thus, in accordance with the invention, the (e.g. plain orifice) nozzle operating in a Rayleigh regime in combination with the first orifices providing the impinging first air streams may enable to define resulting droplet size varying with the inhalation flow, whereby the droplet size decreases with increasing flow, which may provide that $d^2*Q$ (and hence effective dose of the inhalation liquid administered to the users lungs) remains substantially constant. As a result of the interacting first air streams, a propagating velocity component of each of the first air streams is reduced as at least partly opposing velocity components of the first air streams at least partly compensate each other, whereby the turbulences in the first air stream add, resulting in an air stream in the intake duct that exhibits a desired characteristics.

The inhalation air (also referred to as inhalation gas) may comprise any gas or gas mixture, comprising e.g. air, oxygen, helium, nitrogen, etc. The inhalation liquid may comprise any liquid, comprising e.g. a pharmaceutical ingredient, a herbal ingredient, or any other substance. The inhalation airflow may be a forced airflow or may be naturally generated, e.g. by natural inhaling of the user. The inhalation liquid may be injected from a liquid reservoir. The nozzle (also referred to as a spray nozzle) may be any nozzle arranged for providing a stream of fluid droplets and preferably arranged for operating in a Rayleigh domain as explained above. The nozzle may be positioned in the intake duct and/or to discharge the stream of fluid droplets into the intake duct of the mouth piece. The first orifices may be formed by a plurality of separate orifices, each for providing an air stream. Alternatively, a single air inlet may branch into a plurality of air guiding paths, each path thereby discharging into a respective first orifice. The air streams may be supplied from the first orifices by a user of the aerosol generator generating an under-pressure by means of inhalation, by a stream of air (e.g. from a pressurized container) which discharges via the first orifices, or any other suitable means. The intake duct may e.g. discharge into a mouthpiece or be provided with an integral mouthpiece.

The first orifices provide first air streams in mutually colliding discharging directions causing the first air streams to interact with each other. The mutually colliding discharging directions may form mutually facing directions (e.g. with an offset or without offset) or may mutually collide under an angle. For example, the discharging directions may be opposing (i.e. in opposite directions) or partially opposing, i.e. under an angle with respect to each other thereby the directions each having a directional component in opposite direction. The first orifices may be equidistantly spaced apart along an imaginary circle around the droplet train propagation path (i.e. the droplet train propagation path passing through a center of the circle and being perpendicular to a plane in which the circle extends), whereby the discharging directions of the first orifices extend towards the droplet train propagation path (so as to impinge). Such configuration may for example be provided making use of 2, 3, 4, 5, 6, 7, 8 or any other number of first orifices.

The first orifices are positioned for providing the first air streams so as to interact with each other in the droplet train propagation path downstream of the nozzle. The interaction of the first air streams may be provided by the first air streams impinging, rubbing or any other suitable interaction. It will be understood that the interaction of the first air streams is provided downstream of the nozzle, i.e. in (e.g. a part of) the droplet train propagation path. The first air streams from the first orifices are at least partly opposing in that the first air streams from these first orifices are directed towards each other so as to interact, e.g. in opposing directions or under any suitable angle. The first air streams from the first orifices flow, from the respective first orifices, along the respective discharging directions of the respective first orifices (i.e. in respective straight lines) to the droplet train propagation path.

The first orifices may be positioned so that their discharging directions intersect at a point in the droplet train propagation path (a point downstream of the nozzle). As a result, the first air streams propagate along respective straight lines to the droplet train propagation path and provide for the described turbulence in the droplet train propagation path, i.e. at or near the point or area of intersection of the discharging directions.

Likewise, the described turbulence may also be obtained when the first air streams impinge with an offset or rub against each other. Thereto, the first orifices may be positioned so that their projected discharging surfaces along the respective discharging directions intersect at a point in the droplet train propagation path (a point downstream of the nozzle). In an embodiment, the first orifices are arranged for generating the first air stream at an angle of substantially 90 degrees in respect of the droplet train propagation path and having opposing (with or without offset), mutually facing directions, so as to provide a high air speed gradient, which may result in homogeneous turbulence. The homogeneous turbulence may tend to shake the droplets from the nozzles out of their propagation path. The inhalation liquid may comprise a liquid drug substance, a drug substance solved in a solvent, a drug substance forming a suspension or any other suitable form.

A plurality of the first orifices may be provided, the first orifices being arranged along a circle around the droplet train propagation path. By providing e.g. 3, 4, 5, 6, 7, 8 . . . first orifices. More orifices will result in a more rotation symmetric air flow pattern. The smaller the first orifices, the smaller the resulting eddies or re-circulations. For each liquid (with different viscosity, surface tension and density), a different optimum may be found for the number, position and size of first orifices.

In an embodiment, the first orifices are positioned and arranged for generating a homogeneous turbulence in the droplet train propagation path having a length scale in a same order of magnitude as the aerosol droplet size. The term length scale may be understood as a diameter of recirculation in the turbulence. The smallest length scales may be in a same order of magnitude as the aerosol droplet size. This length scale can be interpreted as a diameter of the recirculation: the smallest re-circulations inside the aerosol generator according to the invention, should have a characteristic diameter in a range of 1 micron to 50 microns, preferably 3 microns to 30 microns, more preferably 5-20 microns. Thereby, the smallest characteristic diameter of the re-circulations in the turbulence created, may be in a same order of magnitude as the droplets and the distances between successive primary droplets injected by the Rayleigh nozzle. The distance between subsequent droplets in a Rayleigh nozzle generated droplet train may be approximately 2-3 times the diameter of the primary droplets (2-8 μm), thus in this embodiment corresponding diameters of the desirable recirculation, or length scales, may be 4-24 μm.

In an embodiment, the droplets would just be shaken out of the droplet train. If droplets are between 2 and 8 micron in diameter, a matching length scale may be between 5 and 20 μm.

The inventors found by practical experiments that such homogeneous turbulence may for example be obtained in that a ratio of a distance of an (air) outlet of the first orifices to and the droplet train propagation path in respect of a diameter of the first orifices is chosen in a range from 3:1 to 30:1, preferably in a range of 5:1 to 20:1. The local turbulence intensity at the droplet train propagation path is being caused by the velocity of the air stream from the first orifice and by the local difference between the velocity of the outer bounds of the air stream from the first orifice and the surrounding air. This turbulence intensity needs some travel distance to fully develop. However, if the distance of the first orifices to the droplet train propagation path is too far away, the turbulence fades out, the turbulence intensity decreases. The diameter of the first orifices may have a strong influence on the optimal distance to the droplet train propagation path. Smaller orifices shall be placed closer to the droplet train propagation path to obtain the optimal turbulence intensity.

In an embodiment, the Rayleigh nozzle is arranged for providing primary droplets in a range of 2-8 microns, more preferably in a range of 3-5 microns. A finally resulting average droplet size (after coalescence) may be larger. In an embodiment, the finally resulting average droplet size is between 4 and 7 μm, which may be achieved with the mentioned primary droplets of 3 to 5 μm. In an embodiment, the Rayleigh nozzle is arranged for providing primary droplets of 4 micron (from an orifice of 2 micron diameter). A finally resulting average droplet size (after coalescence) may be between 5 and 9 μm, depending on the inhalation air flow. This range may provide the above-mentioned effect that d^2*Q is substantially constant. Generally, as a diameter of the nozzle is around half a diameter of the primary droplets, in order to provide primary droplets in the above mentioned ranges of 2-8 microns, respectively 3-5 microns, a nozzle diameter of 1-4 microns, respectively 1.5-2.5 microns will be provided.

In an embodiment, the aerosol generator further comprises at least one second orifice for providing a second air stream propagating in a direction of the droplet train propagation path and forming a sheath flow around the droplet train propagation path. The homogeneous turbulence having the desired above characteristics, such as length scale, as obtained from the first orifices may be provided at a low airflow, which may be lower than the flow normally inhaled by a user. A remaining part of the flow inhaled by a user may be obtained via the second orifices. As only a part of the users inhalation flow may be required for generating the turbulence described above, a remainder of the flow normally inhaled by the user may be used for other purpose, such as a sheath flow. The sheath flow may further reduce a deposition of droplets in the aerosol generator as well as in the users mouth.

In an embodiment, a quotient of the inhalation flow from the second air stream from the second orifices and the inhalation flow of the first air stream from the first orifices is at least 1 to 1, preferably at least 2 to 1, more preferably at least 5 to 1. Given a normal inhalation flow as considered comfortable and/or natural by a user, the larger the quotient, the smaller the first air stream via the first orifices, the more homogeneous a turbulence may be, resulting in less large eddies which may cause retention in the inhaler device. The more sheath air, the more distance of the aerosol carrying core flow to the walls, which prevents the turbulent aerosol generated by the first air streams and the Rayleigh nozzle to deposit as wall losses in the inhaler device.

In an embodiment, the Rayleigh nozzle comprises a plurality of orifices for generating a plurality of droplet trains in parallel, comprising at least 10 orifices, preferably at least 50 orifices, more preferably at least 100 orifices. An array of orifices may be provided, each having an orifice diameter in a range of 0.1 to 5 μm, preferably 1.5 to 3 μm, so as to allow to spray a large quantity of fine droplets in order to achieve a desired total dose during the inhalation. The liquid flow rate may be 1 to 50 μl per second, preferably 5 to 30 μl per second, more preferably 6 to 15 μl/s. A heart to heart distance between neighboring orifices may be in a range of 2 to 6 times the orifice diameter so as to reduce a risk of coalescence of neighboring droplets, when subjected to the homogeneous turbulence.

In an embodiment, the Rayleigh nozzle comprises a plurality of orifices for generating a plurality of droplet trains in parallel, comprising preferably at least 10 orifices, more preferably at least 20 orifices, still more preferably at least 50 orifices, even more preferably at least 100 orifices, so that—even with small droplets, a desired quantity of the inhalation liquid may be administered.

To inhale a liquid aerosol with an average particle size of 6 micron or larger into the deeper lung regions, a slow inhalation is vital, well below 30 lpm. Inhaling at less than 7 lpm may be uncomfortable for a user. Inhaling a comfortable volume of 1 liter will take 8.5 seconds at that air speed.

In an embodiment, the first and second orifices are dimensioned to obtain a total inhalation flow passing the first and second orifices of 30 liters per minute or less, preferably 7-20 liters per minute. The inventors have performed extensive usability studies with moderate to high airflow resistances (15 lpm air flow at −2 kPa under-pressure, 15 lpm at 4 kPa under-pressure and 15 lpm at 6 kPa under-pressure).

In an embodiment, an air stream of the sheath flow is homogeneously turbulent (substantially free from large eddies) or laminar. Thereby, a substantial mixing of the sheath flow with the primary air flow from the first orifices that may contain the droplets of the inhalation liquid, may be prevented, so that deposition of the inhalation liquid on the walls of the inhalation duct may be reduced.

In an embodiment, the second orifices are provided with at least one of a labyrinth and laminating vanes, which may provide that the sheath flow is free of large eddies (homogeneously turbulent or laminar).

In an embodiment, no obstacle is provided from the nozzle to an inhalation outlet of the aerosol generator so as to provide a substantially free propagation path from the nozzle to the inhalation outlet, which may tend to reduce a depositing of the aerosol in the aerosol generator.

In an embodiment, the first orifices are formed by atmospheric orifices. i.e. orifices having an inlet which draws in air from an ambient environment (i.e. ambient air). In the atmospheric orifices The air is drawn in in that under-pressure is applied to the intake duct (e.g. by a user inhaling), causing a pressure difference between inlet and outlet of the first orifices. The term under-pressure (also identified in this document as underpressure) is to be understood as a pressure which is lower than atmospheric or ambient pressure. The term under-pressure may also be understood as or realized by the application of a suction force.

In accordance with the compensation effect as described above, in an embodiment, the aerosol generator is constructed for increasing a turbulence of the interacting first air streams in the droplet train propagation path, with an increasing inhalation under-pressure, thereby decreasing a droplet size with increasing inhalation under-pressure. The aerosol generator may further be constructed for decreasing a droplet size with increasing inhalation under-pressure to such an extent so as to at least partly compensate for an increasing throat deposition with increasing inhalation under-pressure, which allows for providing a substantially constant dose to the lungs of a user over a range of inhalation under-pressures, thereby variations in throat deposition and particle size as a result of varying inhalation under-pressure at least partly compensating each other.

Using slightly different wording, the above invention may generally also be phrased as an aerosol generator for generating an inhalation aerosol from an inhalation liquid, comprising:

an intake duct for guiding air to a mouth of a user, and a nozzle, arranged for injecting the inhalation liquid into the intake duct, wherein the nozzle is arranged for generating a Rayleigh droplet train of the inhalation liquid propagating along a droplet train propagation path, and wherein the intake duct comprises:

at least two first orifices having at least partly opposing discharging directions extending towards the droplet train propagation path, the at least two first orifices being configured for providing respective first air streams in opposing directions so as to interact in the droplet train propagation path.

The same effects as described above apply, and the same or similar preferred embodiments may be provided, providing the same or similar effects.

The aerosol generator according to the invention may be applied in an inhaler. Accordingly, according to an aspect of the invention, there is provided an inhaler for inhaling an inhalation liquid, the inhaler comprising an aerosol generator according to the invention, and a container for holding an amount of the inhalation liquid, the container having a discharging opening that is connected to a supply opening of the nozzle of the aerosol generator for supplying inhalation liquid to the nozzle. The container may comprise a cartridge, a flexible container or any other reservoir. The aerosol generator and/or the container may be disposable. The inhalation liquid as held by the container may comprise a medicine or any other substance. The container may hold a quantity of the inhalation liquid sufficient for a plurality of administrations of the inhalation liquid, e.g. 30, 60 or 90 administrations.

According to a further aspect of the invention there is provided a method of testing an aerosol generator according to the invention, the method comprising:

connecting an intake duct of the aerosol generator to an under-pressure duct;

applying via the under-pressure duct an under-pressure to the aerosol generator;

generating by a nozzle of the aerosol generator a Rayleigh droplet train along a droplet train propagation path of the aerosol generator;

providing, in response to the under-pressure, by at least two first orifices of the aerosol generator respective first air streams, the first orifices having at least partly opposing discharging directions, the respective first air streams flowing from the respective orifices along the respective discharging directions to the droplet train propagation path so as to interact in the droplet train propagation path;

changing a pressure level of the under-pressure;

measuring a parameter of the aerosol generated by the aerosol generator at at least two different under-pressure levels;

deriving a test result from a comparison of the parameter as measured at the different under-pressure levels.

Thus, a testing of the aerosol generator in accordance with the invention may be performed by varying a suction (under-pressure) as applied to the inhalation duct, or mouthpiece, and measuring a parameter (e.g. average droplet size, deposition or other suitable parameter as will follow in more detail below) of the aerosol that is generated. As explained above, the aerosol generator according to the invention may provide that a droplet size of the inhalation liquid varies in dependency of the inhalation flow, which enables to at least partly compensate an effect of a smaller droplet size and an effect of a larger inhalation flow against each other.

The parameter may be a droplet size, the testing may accordingly comprise measuring a droplet size in the inhalation aerosol at a plurality (at least two) of different inhalation flows, and determining if the a droplet size decreases with an increase in inhalation flow. A test result is derived from a comparison of the measured droplet size at the different inhalation under-pressure levels. In case of sufficient decrease, e.g. the decrease of the particle size upon an increase in inhalation flow being in a predetermined range (e.g. a range that in practice results in the above described compensation effect), the aerosol generator may be considered to have passed the test. The droplet size may be measured making use of laser diffraction measurement or an aerodynamic particle sizer. A "test passed" test result may be assigned to the aerosol generator when a decrease in the droplet size at an increasing under-pressure level is in a predetermined droplet size test pass band Alternatively, the droplet size may be measured indirectly. Accordingly, in an embodiment, the under-pressure is applied to the aerosol generator via a mechanical throat model (comprising e.g. a so called Alberta throat as developed at Alberta University) comprising a throat modelling section that models a throat of a user of the aerosol generator and a filter, downstream of the throat modelling section for deposition of the aerosol that has passed the throat modelling section, the parameter being the droplet size of the aerosol generated by the aerosol generator, the method indirectly measuring the droplet size by measuring a quantity of a deposition of the aerosol in the filter, and deriving a test result from a comparison of the quantity of the deposition in the filter for the at least two under-pressure levels. Using the model of the throat, a deposition of the aerosol may be measured at different inhalation flows. Such indirect measurement may be provided as a relation between droplet size, inhalation flow and losses due to deposition in the throat of the model is known. Thus, it may be tested if the above described compensation effect occurs to a sufficient degree, as at a larger inhalation flow, deposition in the mechanical throat will increase while droplet size will decrease, providing the at least partly compensation so as to result in a substantially constant or more constant deposition at different inhalation flows.

Accordingly, in an embodiment, a "test passed" test result is assigned to the aerosol generator when a difference in the deposition at different under-pressure levels remains within predetermined deposition test pass band (thus being relatively constant).

BRIEF DESCRIPTION OF THE DRAWINGS

Further advantages, features and effects of the invention will become clear from the appended drawing, showing non limiting embodiment, wherein.

DETAILED DESCRIPTION OF THE INVENTION

Figure 1:
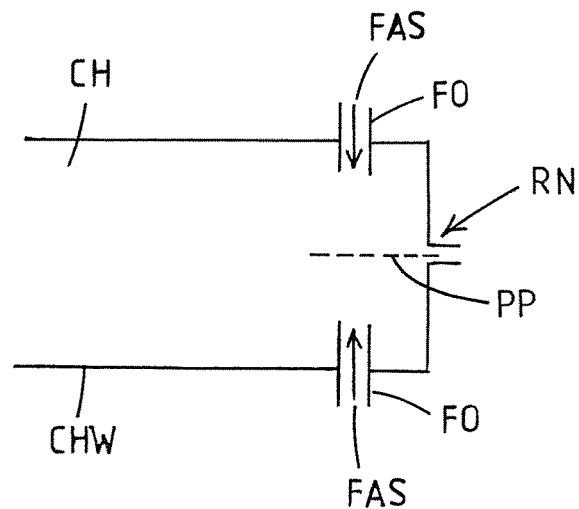
FIG. 1 depicts a schematic, partly cross sectional view of an aerosol generator according to an embodiment of the invention.

FIG. 1 depicts a schematic view of a aerosol generator of a liquid inhaler device comprising an intake duct CH formed by intake duct wall CHW. A Rayleigh nozzle RN is provided at an end of the intake duct. Fine droplets of an inhalation liquid are injected by the Rayleigh nozzle and propagate away from the nozzle along a propagation path PP. An outlet is provided at an opposite end of the intake duct. Mutually facing first orifices FO lead into the intake duct. When a user inhales via the outlet of the intake duct, air is drawn in via the first orifices thereby generating first air streams FAS, discharging directions of the first orifices being indicated by the arrows indicating the first air streams FAS. The first air streams interact, i.e. in this example impinge in an area of the intake duct through which the propagation path passes. Although FIG. 1 depicts two first orifices, a larger number of first orifices may be provided, for example arranged along a circle, whereby the first orifices are posited equidistantly around the propagation path and impinge at (a point in) the propagation path. The plurality of first orifices may for example be positioned so as to provide respective first air streams that pair wise have opposite directions. The impinging first air streams may result in a homogeneous turbulence in the area of impingement where the injected droplets propagate. As a result, the injected droplets are moved (distributed) somewhat sideways from the propagation path. An aerosol AS is thereby provided that propagates to the outlet of the duct CH. Given the nature of the homogeneous turbulence and the small length scale of the circulations in the order of for example 10 microns with primary droplets having a size of approximately 4 microns.

Figure 2:
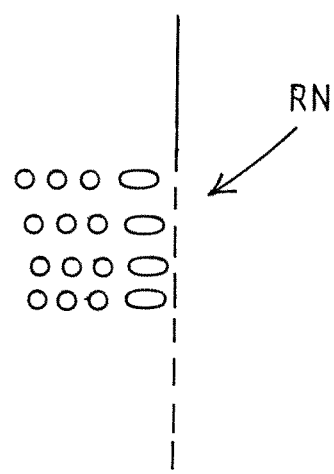
FIG. 2 depicts a schematic side view of a nozzle and droplet train of a aerosol generator according to an embodiment of the invention.

As depicted in FIG. 2, the Rayleigh nozzle RN may comprise a plurality of orifices arranged in a planar (matrix) configuration, so that a plurality of droplet trains are injected. The Rayleigh nozzle may comprise a substrate, such as a silicon substrate, into which a plurality of small orifices are provided, for example by means of any suitable silicon etching technique.

Figure 3:
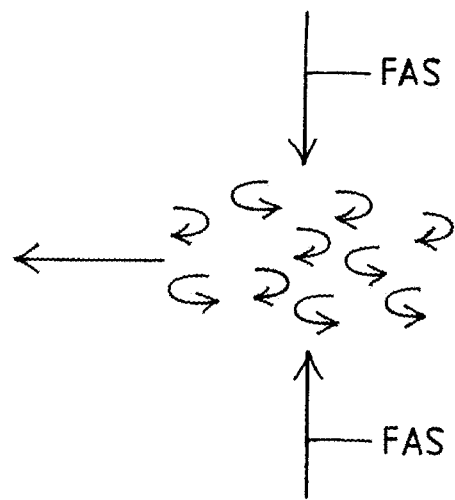
FIG. 3 depicts a schematic side view of a first air stream in a aerosol generator according to an embodiment of the invention.

FIG. 3 depicts a highly schematic, simplified representation of an example of the turbulence that may occur in the area A where the first air streams FAS impinge. The droplet train of droplet trains, such as for example depicted in and described with reference to FIG. 2, pass through this area. Due to the turbulence, the droplets will be shaken out of their respective droplet train. As a result, collisions of sequential droplets in the same droplet train may be reduced so that coalescence may be reduced, thereby reducing an increase in droplet size. Given the small length scale of the turbulence vortices, collisions between droplets of "neighbour" droplet trains may be kept at a low level. Furthermore, the properties of the homogeneous turbulence tend to depend on a magnitude of the inhalation flow: the higher the inhalation flow, hence the higher the flow of the first air streams, the stronger the turbulence in the area A may be, which may translate into more droplets being moved out of their droplet train position. As a result, at a higher inhalation flow, less collisions may occur, which may translate into a smaller effective droplet size. As the primary droplet size (i.e. the droplet size of the droplets that leave the Rayleigh nozzle) is relatively constant, the droplet size of the droplets leaving the aerosol generator, may exhibit a dependency on the turbulence level and hence on the inhalation air speed: thereby, a compensation effect may be obtained which results in a more constant lung deposition, relatively independent on magnitude of the inhalation flow, as will be explained below.

As cited above, the deposition in the upper respiratory system (mouth, throat, etc) may be proportional to $d^2*Q$, wherein d is a diameter of the droplets and Q is the inhalation flow. In accordance with the invention, the Rayleigh nozzle in combination with the first orifices providing the first air streams may enable to define resulting droplet size varying with the inhalation flow, whereby the droplet size decreases with increasing flow, which may provide that $d^2*Q$ (and hence effective dose of the inhalation liquid administered to the users lungs) remains substantially constant. Thus, the nozzle in combination with the first orifices in accordance with the invention, may provide that a coalescence of droplets is relatively strongly varying with inhalation flow, so that an effect of inhalation flow on effective deposition in the lung of the user, may to a large extent be compensated by an effect the changed inhalation flow has on coalescence of droplets, hence on an effective droplet size.

Figure 4:
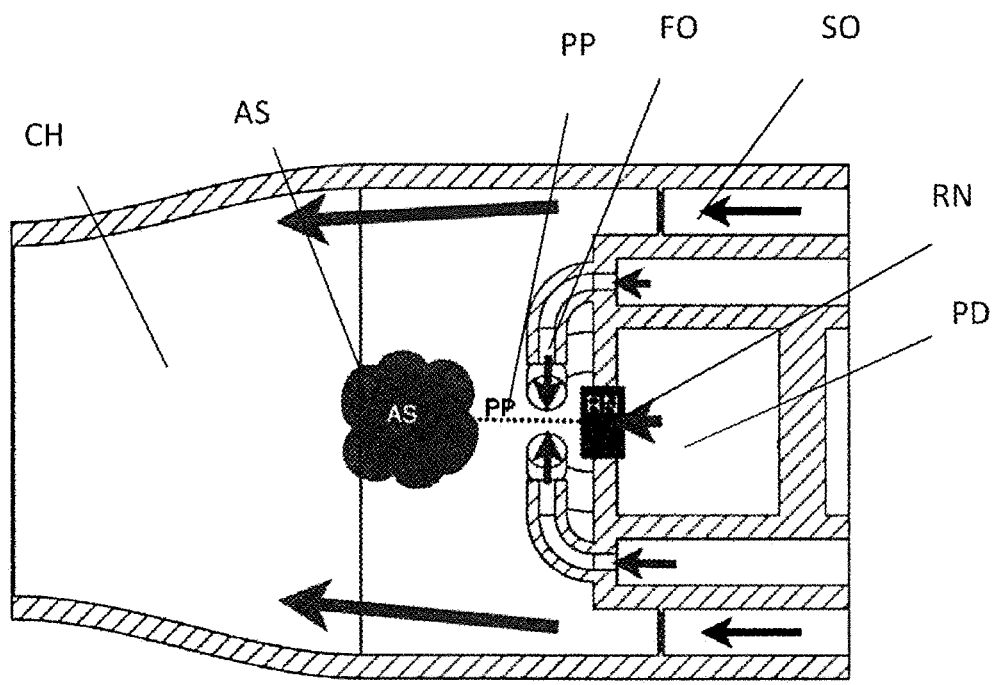
FIG. 4 depicts a schematic cross sectional side view of a aerosol generator in according to an embodiment of the invention.

FIG. 4 depicts another example of a aerosol generator according to an embodiment of the invention. FIG. 4 depicts a liquid inhaler device comprising, likewise to the liquid inhaler device depicted in and described with reference to FIG. 1, an inhalation duct CH (also referred to as intake duct CH) in which a Rayleigh nozzle RN injects a droplet train or a plurality of droplet trains from a pressurizing device PD (such as in this example a pressurized reservoir). The droplet train(s) is resp. are subjected to a turbulence generated by the impinging first air streams FAS which may have an effect as described above. As a total flow of the resulting aerosol AS provided via the first air streams may be lower than a flow which would be considered by a patient to be a natural inhaling, additional inhalation air may be provided by means of the second orifices SOF that provide a second air stream SAS that may form a sheath flow around the aerosol AS. A magnitude of the second air stream may be defined by second air stream inlet openings SIO that enable air to flow into the second orifices. In order to make the second air stream more homogeneous, a filter mesh FM may be provided in the second orifice and/or in the second air stream from the second orifice, thereby for example reducing large eddy air streams. Alternatively, laminating vanes or a labyrinth could be provided in the second orifice and/or in the second air stream from the second orifice to achieve such result.

Figure 5A:
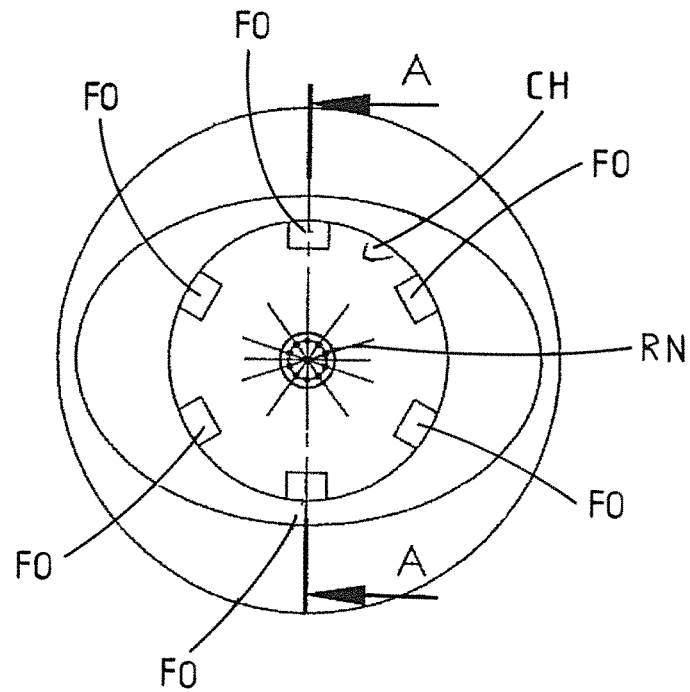
FIG. 5A-5C depict a cross sectional front view, side view and side view in use of an inhaler comprising an aerosol generator according to an embodiment of the invention.

FIG. 5A depicts a front view of a liquid inhaler device showing a view into the intake duct CH. In this embodiment, six first orifices are provided pair wise facing each other. The six orifices being substantially equidistantly arranged substantially circularly symmetric in respect of the nozzle RN. Although in this example six first orifices are depicted, generating six first air streams, other embodiments may apply two, three, four, or any other preferably even or odd number of first nozzles. At an outlet of the intake duct CH, the housing of the aerosol generator may be provided with an oval shape to allow easy application in a users mouth.

Figure 5B:
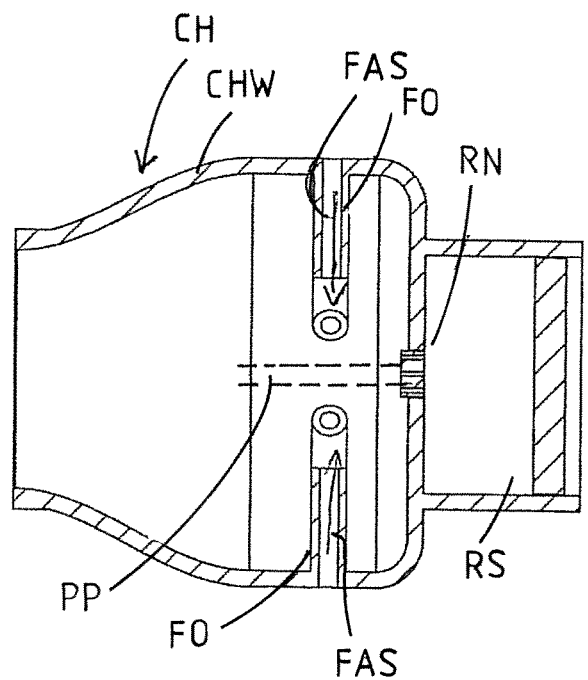

A cross sectional view of the aerosol generator of the inhaler in accordance with FIG. 5A, along the line A-A, is depicted in FIG. 5B. FIG. 5B depicts intake duct CH formed by intake duct wall CHW. Rayleigh nozzle RN is provided at an end of the intake duct. A reservoir RS is provided (which may be pressurized thereby forming an embodiment of a pressurizing device to pressurize the inhalation liquid) from which the to be injected liquid is provided to the nozzle RN via a discharge opening of the reservoir. The reservoir may also be referred to as a container. The reservoir may form an integral part of the inhaler device or may be a replaceable, e.g. disposable, reservoir, such as a cartridge, that contains an amount of the inhalation liquid, e.g. for 30, 60 or 90 inhalation administrations The mutually facing first orifices FO lead into the intake duct CH. When a user inhales via the outlet of the intake duct, air is drawn in via the first orifices FO thereby generating first air streams FAS. The first air streams interact (e.g. impinge) in an area of the intake duct through which the propagation path PP passes.

Figure 5C:
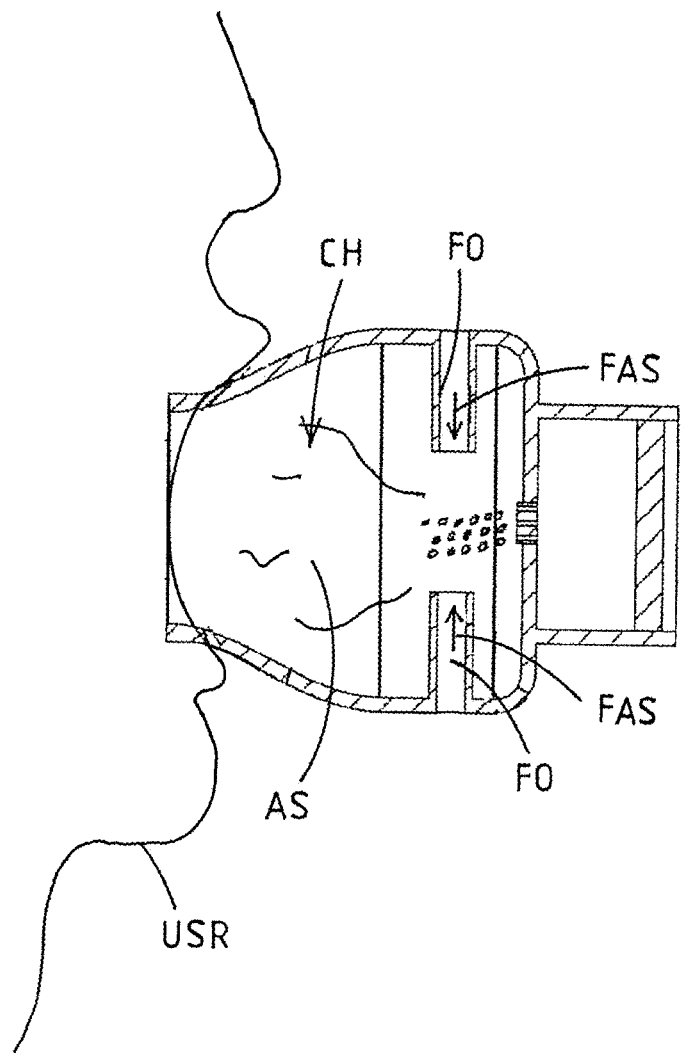

FIG. 5C depicts a view of a aerosol generator similar to the one depicted in FIG. 5B, however in the example depicted in FIG. 5C having 2 first orifices, while in the example depicted in FIG. 5B having 6 first orifices. In FIG. 5C, the aerosol generator is applied to a users USR mouth. As the user inhales via the outlet of the intake duct, air is drawn in via the first orifices thereby generating first air streams FAS. The first air streams impinge in an area of the intake duct through which the propagation path passes. The impinging first air streams may result in a homogeneous turbulence in the area of impingement where the injected droplets propagate. As a result, the injected droplets are distributed to some extent out of the propagation path. An aerosol AS is thereby provided that propagates to the outlet of the duct CH and into the users mouth.

Figures 6, 7:
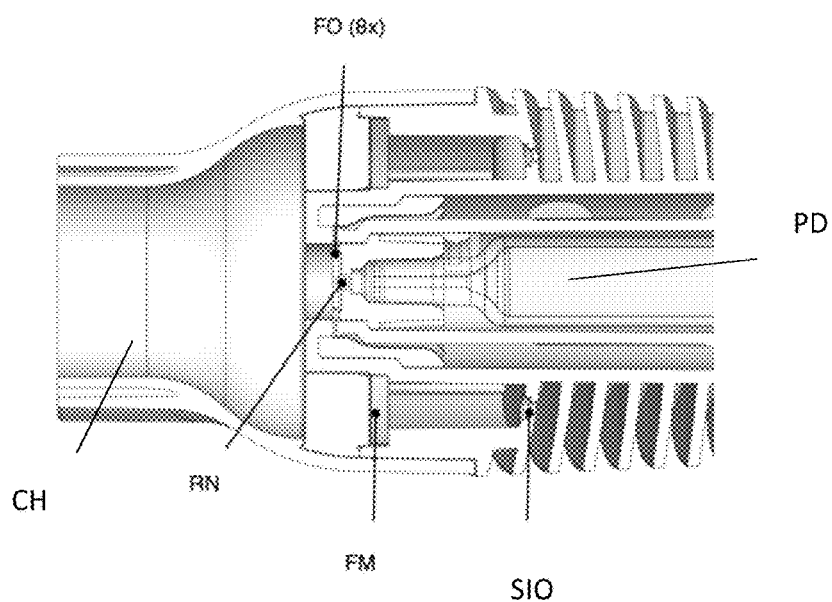
FIG. 6 depicts a table of the average droplet size (MMAD, mean mass aerodynamic diameter) at different inhalation air flow rates, where $d^2*Q$ remains practically constant.
FIG. 7 depicts a cross sectional view of a liquid inhaler device according to an embodiment of the invention.

FIG. 6 is a table with measured MMADs at different air flows, mean mass aerodynamic diameter, the average droplet size, from a prototype of an embodiment of the liquid inhaler according to the invention. The inhaler has an air flow resistance of 15 lpm at 2 kPa underpressure. Users inhaling at pressures P of −1, −2 or −3 kPa as depicted in the top row of the table, inhale at the corresponding air flows Q as depicted in the second row of the table. Corresponding mean mass aerodynamic diameter (MMAD) is depicted in the third row. The table shows in the $4^{th}$ row that $d^2 \ast Q$ remains substantially constant, which may predict a similar lung dose at different air flow rates.

FIG. 7 depicts another example of a aerosol generator of a liquid inhaler device according to an embodiment of the invention. FIG. 7 depicts a liquid inhaler device comprising, likewise to the liquid inhaler device depicted in and described with reference to FIGS. 1 and 4, an inhalation duct CH (also referred to as intake duct CH) in which a Rayleigh nozzle RN injects by a pressurizing device PD which pressurizes the inhalation liquid, a droplet train or a plurality of droplet trains on a droplet train propagation path PP. The droplet train(s) is resp. are subjected to a turbulence generated by the interacting first air streams FAS which may have an effect as described above. The version depicted here, has 8 first air streams. As a total flow of the resulting aerosol AS provided via the first air streams (e.g. 40 ml/s) may be lower than a flow which would be considered by a patient to be a natural inhaling (>150 ml/s), additional inhalation air may be provided by means of the second orifices SO that provide a second air stream that may form a sheath flow around the aerosol AS. A magnitude of the second air stream may be defined by second air stream inlet openings SIO that enable air to flow into the second orifices. In order to make the second air stream more homogeneous, a filter mesh FM may be provided in the second air stream, thereby for example reducing large eddy air streams.

Figure 8:
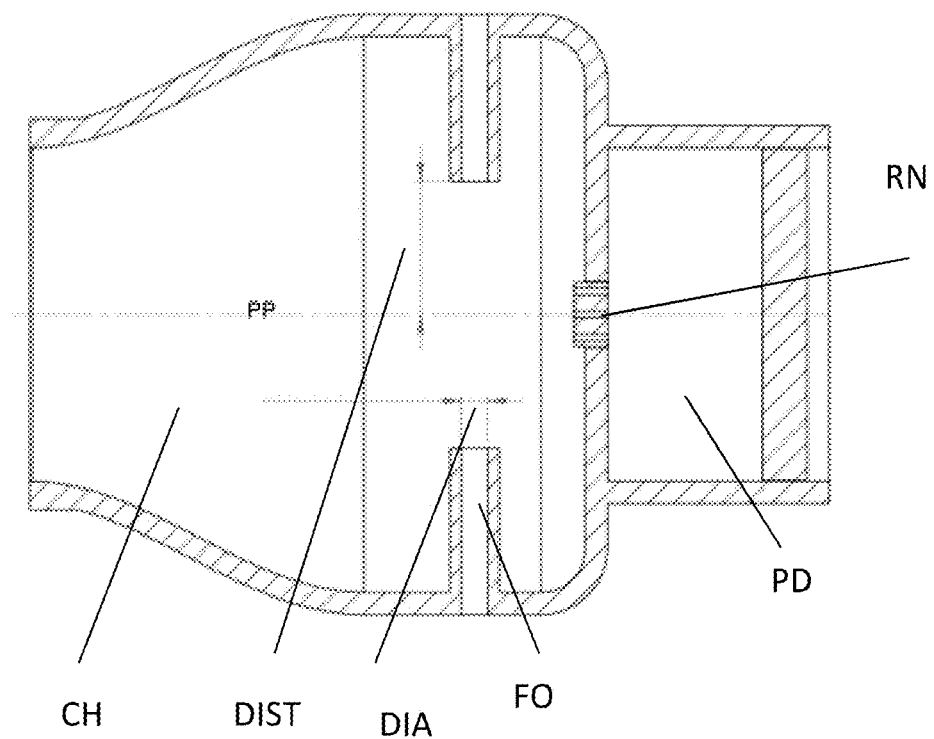
FIG. 8 depicts a cross sectional detail view of the first air inlets generating the at least two first air streams and their dimensioning.

FIG. 8 depicts a detail view of the first orifices FO generating the at least two first air streams and their dimensioning. The first air inlets may generate a homogeneous turbulence if a ratio of a distance DIST of an air inlet orifice which generates a first air stream, to the droplet train propagation path PP in respect of a diameter DIA of the orifice FO is chosen in a range from 3:1 to 30:1, preferably in a range of 5:1 to 20:1.

Figure 9:
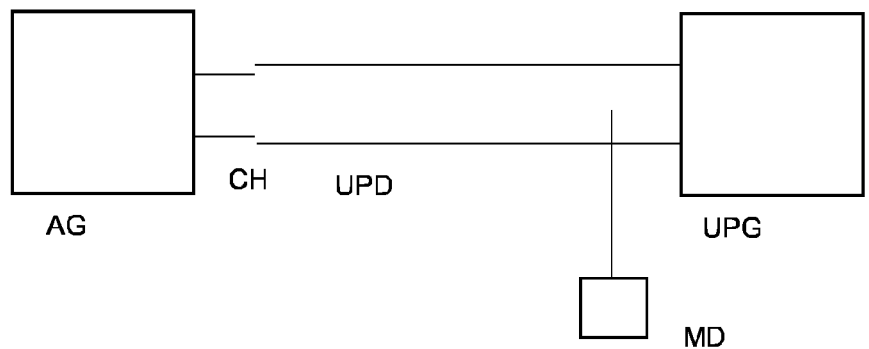
FIG. 9 schematically depicts an example of a test arrangement based on which an embodiment of the testing method according to the invention will be described.

FIG. 9 depicts a testing arrangement for testing an aerosol generator according to an embodiment of the invention, in order to illustrate the method for testing an aerosol generator according to the invention. FIG. 9 accordingly depicts an aerosol generator AG, such as the aerosol generators as described with reference to FIGS. 1-8. An intake duct CH of the aerosol generator is connected (e.g. via a suitable coupling, such as a resilient coupling) to an under-pressure duct. The under-pressure duct leads to an under-pressure generator UPG, such as a suction device, a pump, etc. The testing arrangement comprises a measurement device MD that measures a parameter, such as a size of the droplets in the aerosol.

In operation, the under-pressure generator will apply an under-pressure to the under-pressure duct, hence to the intake duct of the aerosol generator. The nozzle of the aerosol generator will inject droplets which propagate along the droplet train propagation path, as described above with reference to FIG. 1-8. As a result, the first air streams will interact with the droplets in the droplet train propagation path, resulting in turbulence as described above causing the droplets in the droplet train to be shaken out of their path to some extent. A parameter of the aerosol thus generated in the under-pressure duct is measured by the measurement device. The parameter may e.g. be a droplet size. The measurement device may comprise a laser diffraction measurement or an aerodynamic particle sizer. Then, the under-pressure level is altered, for example by increasing or decreasing an under-pressure level, thereby simulating a corresponding larger or smaller air inhalation by a user. The measurement (of e.g. particle size) is repeated.

As explained above, the aerosol generator according to the invention may provide that a droplet size of the inhalation liquid varies in dependency of the inhalation flow, which enables to at least partly compensate an effect of a smaller droplet size and an effect of a larger inhalation flow against each other.

In the example where the parameter is a droplet size, the testing may accordingly comprise measuring a droplet size in the inhalation aerosol at a plurality (at least two) of different inhalation flows, and determining if the a droplet size decreases with an increase in inhalation flow. A test result is derived from a change of the measured droplet size at the different under-pressure levels. In case of a decrease of the particle size upon an increase in inhalation flow being in a predetermined range (e.g. a range that in practice results in the above described compensation effect), the aerosol generator may be considered to have passed the test.

Figure 10:
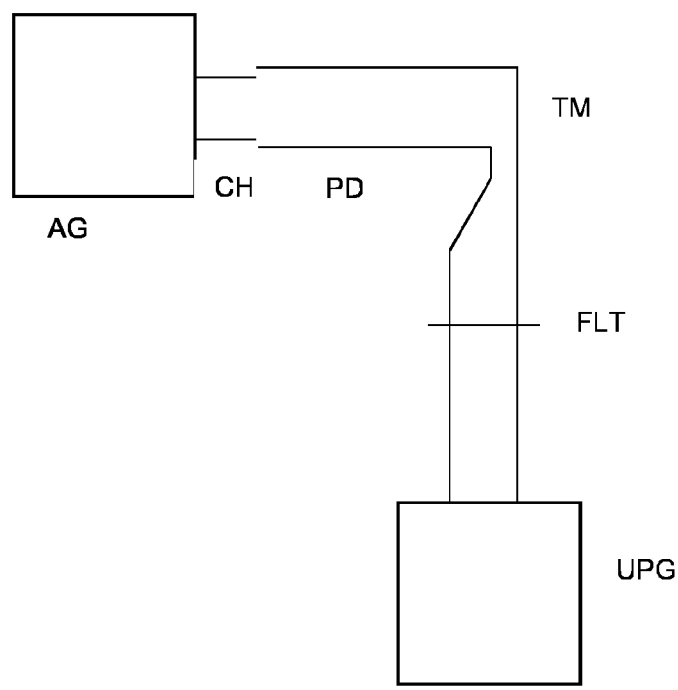
FIG. 10 schematically depicts another example of a test arrangement based on which an embodiment of the testing method according to the invention will be described.

FIG. 10 depicts another embodiment of a testing arrangement for testing an aerosol generator according to an embodiment of the invention, in order to illustrate the method for testing an aerosol generator according to the invention. In FIG. 10, the aerosol generator AG having intake duct CH, the under-pressure duct UPD and the under-pressure generator UPG are depicted likewise to FIG. 9. Furthermore, a mechanical throat model TM is provided, such as an Alberta throat model as developed by Alberta University. The throat model models the curves, narrow parts etc. in e.g. a typical human throat. A filter FLT is provided downstream of the throat model TM in order to absorb the droplets that have passed the mechanical throat model TM. Given the bends and narrowing, a deposition of droplets from the aerosol in the model of the throat will to a large extent correspond with that in a human throat.

A deposition of the aerosol in the filter FLT is now measured at different inhalation, by setting the under-pressure to a certain level, generating the aerosol by the aerosol generator, measuring a deposition in the filter, and repeating the same at another under-pressure level. The deposition at the different under-pressure levels is compared. Thereby, it may be tested if the above described compensation effect occurs to a sufficient degree, as at a larger inhalation flow, deposition in the mechanical throat will increase while droplet size will decrease, providing the at least partly compensation so as to result in a substantially constant or more constant deposition in the lungs of a user (hence in the filter of the test setup) at different inhalation flows. The measurement of the deposition thus indirectly measures the droplet size, as droplet size, deposition and inhalation flow of the throat model are related to each other. Accordingly, a "test passed" test result is assigned to the aerosol generator when a change in the deposition at different under-pressure levels remains within a predetermined deposition test pass band (thus being relatively constant).

When testing the aerosol generator, the average particle size (MMAD, mean mass aerodynamic diameter) should be smaller at higher air flow rates and larger at lower air flow rates, ideally following a constant $D^2*Q$ where D is the average droplet diameter and Q the air flow, in order for the aerosol generator to achieve a constant deposition in the lungs of the patient. Thus, when measuring the droplet size as a function of the air flow rate (under-pressure level), an ideal change of the droplet size as a function of the changed air flow rate may be derived from the formula: $D^2*Q$=constant. As a test criterion, an average in vitro lung dose fluctuation of ±25%, preferably ±15% may be applied as a maximum allowable difference over a user inhalation air flow range.

The invention claimed is:

1. An aerosol generator for generating an inhalation aerosol from an inhalation liquid, comprising:
    an intake duct having an outlet for guiding air to a mouth of a user and having an inlet allowing ambient air to be drawn in as the user inhales though the device; and
    a nozzle, arranged for generating a Rayleigh droplet train of droplets of said inhalation liquid and for injecting said droplet train into the intake duct along a droplet train propagation path,
    wherein the intake duct comprises at least two first orifices, communicating with said inlet, each of the first orifices having a discharging direction in which, during operation, a respective first air stream discharges from one of the at least two first orifices into said intake duct in a direction that crosses said droplet train propagation path;
    wherein the intake duct comprises at least one second orifice, in communication with said inlet, said second orifice having a discharge direction in which, during operation, a second air stream enters said intake duct substantially in a longitudinal direction to said outlet of said intake duct; and
    wherein the first orifices are arranged to release the respective first air streams in mutually crossing discharge directions, directed towards and into the droplet train propagation path, so as to interact with each other and with said droplets in said droplet train along said droplet train propagation path downstream of said nozzle.

2. The aerosol generator according to claim 1, wherein the at least two first orifices are configured for generating the first air streams at an angle in a range of 30 to 150 degrees in respect of the droplet train propagation path and having opposing, mutually facing directions, the first air streams propagating at said angle into the droplet train propagation path.

3. The aerosol generator according to claim 2, wherein said angle is substantially 90 degrees.

4. The aerosol generator according to claim 1, wherein the at least two first orifices are configured for generating the first air streams to mutually impinge in the droplet train propagation path, the first air streams propagating from the at least two first orifices at mutually impinging directions into the droplet train propagation path.

5. The aerosol generator according to claim 1, wherein the at least two first orifices are arranged along at least one circle around the droplet train propagation path and configured to generate the first air streams in pairwise opposing directions, the aerosol generator being configured to provide that the first air streams propagate in pairwise opposing directions into the droplet train propagation path.

6. The aerosol generator according to claim 1, wherein a ratio of a distance of an outlet of the at least two first orifices to the droplet train propagation path in respect of a diameter of the at least two first orifices is in a range of 3:1 to 30:1.

7. The aerosol generator according to claim 1, wherein the at least two first orifices are arranged for generating a homogenous turbulence in the droplet train propagation path having a length scale in a range of 1-50 µm.

8. The aerosol generator according to claim 1, wherein the nozzle is arranged for providing primary droplets in a range of 2-12 microns.

9. The aerosol generator according to claim 1, wherein a ratio of the magnitude of the second air stream from the at least one second orifice and the magnitude of the first air streams from the first orifices is at least 2 to 1.

10. The aerosol generator according to claim 1, wherein the nozzle comprises a plurality of at least five nozzle orifices for generating a plurality of Rayleigh droplet trains substantially in parallel.

11. The aerosol generator according to claim 1, wherein the at least two first orifices and the at least one second orifice are dimensioned to obtain a total inhalation flow passing the first and second orifices of 7-20 liters per minute at inhalation underpressures ranging from 1 to 4 kPa.

12. The aerosol generator according to claim 1, wherein the second air stream creates a sheath flow that is homogeneously turbulent or laminar.

13. The aerosol generator according to claim 1, wherein the at least one second orifice is provided with at least one of a vane or a labyrinth for generating laminar flow.

14. The aerosol generator according to claim 1, wherein the at least one second orifice is provided downstream of the inlet with a fine filter mesh, filtering large eddies, with a diameter of smaller than 300 micrometers.

15. The aerosol generator according to claim 1, wherein no obstacle is provided from the nozzle to an inhalation opening of the aerosol generator.

16. The aerosol generator according to claim 1, wherein the at least two first orifices are atmospheric orifices.

17. The aerosol generator according to claim 1, wherein the aerosol generator is constructed for increasing a turbulence of the interacting first air streams in the droplet train propagation path, with an increasing inhalation under-pressure, thereby decreasing a droplet size with increasing inhalation under-pressure.

18. The aerosol generator according to claim 17, wherein the aerosol generator is constructed for decreasing a droplet size with increasing inhalation under-pressure to such an extent so as to at least partly compensate for an increasing throat deposition with increasing inhalation under-pressure.

19. The aerosol generator according to claim 1, being configured for providing the first air streams to flow from the respective first orifices along the respective mutually colliding discharging directions in straight lines into the droplet train propagation path.

20. The aerosol generator according to claim 1, being configured for providing the first air streams to interact with each other at an intersection of the discharging directions in the droplet train propagation path.

21. An aerosol generator for generating an inhalation aerosol from an inhalation liquid, comprising:
   an intake duct having an outlet for guiding air to a mouth of a user and having an inlet for allowing ambient air to be drawn in while the user inhales through the device, and
   a nozzle, arranged for injecting the inhalation liquid into the intake duct,
   wherein the nozzle is arranged for generating a Rayleigh droplet train of the inhalation liquid propagating along a droplet train propagation path, and
   wherein the intake duct comprises:
   at least two first orifices, each of the at least two first orifices having a discharging direction in which respective first air streams discharge from the respective first orifices, wherein the at least two first orifices are arranged to provide the first air streams in mutually colliding discharging directions, the discharging directions of the at least two first orifices being directed towards the droplet train propagation path, the at least two first orifices being configured for providing the respective first air streams to flow from the respective first orifices along the respective mutually colliding discharging directions to and into the droplet train propagation path so as to interact with each other and with the droplet train in the droplet train propagation path,
   at least one second orifice having a discharge direction in which a second air stream discharges into said intake duct substantially in a longitudinal direction to said outlet of said intake duct;
   wherein both said at least two first orifices and said at least two second orifice communicate with said inlet;
   wherein a droplet size decreases with increasing air flow, and
   wherein the discharging directions of the at least two first orifices intersect with the droplet train propagation path at an intersection located downstream of the nozzle and before the outlet of the intake duct.

22. The aerosol generator according to claim 21, wherein the first air streams flow from the at least two first orifices in the respective discharging directions along straight lines into the droplet train propagation path.

* * * * *